United States Patent
Georgeson et al.

(10) Patent No.: US 7,703,327 B2
(45) Date of Patent: Apr. 27, 2010

(54) APPARATUS AND METHOD FOR AREA LIMITED-ACCESS THROUGH TRANSMISSION ULTRASONIC INSPECTION

(75) Inventors: Gary E. Georgeson, Federal Way, WA (US); Michael D. Fogarty, Auburn, WA (US); Richard Bossi, Renton, WA (US)

(73) Assignee: The Boeing Company, Chicago, IL (US)

(*) Notice: Subject to any disclaimer, the term of this patent is extended or adjusted under 35 U.S.C. 154(b) by 1185 days.

(21) Appl. No.: 10/943,068

(22) Filed: Sep. 16, 2004

(65) Prior Publication Data

US 2006/0053891 A1    Mar. 16, 2006

(51) Int. Cl.
*G01N 29/00*    (2006.01)
*A61B 8/00*    (2006.01)

(52) U.S. Cl. .............. 73/624; 73/634; 73/641; 600/447

(58) Field of Classification Search .......... 73/624, 73/634, 639, 643, 644, 640, 641; 600/443, 600/444, 647
See application file for complete search history.

(56) References Cited

U.S. PATENT DOCUMENTS

| | | | |
|---|---|---|---|
| 3,363,227 A | | 1/1968 | Massa |
| 3,959,770 A | * | 5/1976 | Schaefer ............ 714/715 |
| 4,165,649 A | * | 8/1979 | Greer, Jr. ............ 73/644 |
| 4,167,880 A | | 9/1979 | George |
| 4,271,490 A | * | 6/1981 | Minohara et al. ........ 367/122 |
| 4,311,052 A | | 1/1982 | Jeffras et al. |
| 4,366,713 A | * | 1/1983 | Gilmore et al. ............ 73/618 |
| 4,431,936 A | | 2/1984 | Fu et al. |
| 4,433,399 A | * | 2/1984 | Massa ............ 367/157 |
| 4,848,159 A | * | 7/1989 | Kennedy et al. ............ 73/641 |
| 5,329,202 A | * | 7/1994 | Garlick et al. ............ 310/334 |
| 5,488,955 A | * | 2/1996 | Dias ............ 600/459 |
| 5,593,633 A | | 1/1997 | Dull et al. |
| 5,698,787 A | * | 12/1997 | Parzuchowski et al. ....... 73/643 |

(Continued)

FOREIGN PATENT DOCUMENTS

JP           9229911 A        9/1997

OTHER PUBLICATIONS

*Automated Ultrasonic Scanning System (AUSS®), Mobile Automated Scanner (MAUS®)* http://www.engineeringatboeing.com/mfgquality/quality/automatedsystems.html, Jun. 21, 2004, 4 pages.

(Continued)

*Primary Examiner*—J M Saint Surin
(74) *Attorney, Agent, or Firm*—Alston & Bird LLP

(57) ABSTRACT

An apparatus and method for inspecting a structure are provided which include receiving probes and area transducers disposed proximate opposite surfaces of a structure under inspection. An area transducer uniformly emits ultrasonic signals over an area which may be scanned by a receiving probe without corresponding movement of the area transducer. An area transducer may be moved over the surface of the structure or repositioned to provide additional inspection area for the receiving probe to scan, including to provide for continuous inspection. Multiple area transducers may be used in sequence to provide for continuous inspection. Multiple receiving probes may be used, independently or collectively as an array, to increase inspection of a structure, taking advantage of the large area of ultrasonic signals emitted by one or more area transducers.

41 Claims, 3 Drawing Sheets

U.S. PATENT DOCUMENTS

| | | | |
|---|---|---|---|
| 5,814,731 A * | 9/1998 | Alexander et al. | 73/644 |
| 5,824,908 A * | 10/1998 | Schindel et al. | 73/632 |
| 5,902,935 A | 5/1999 | Georgeson et al. | |
| 6,484,583 B1 * | 11/2002 | Chennell et al. | 73/623 |
| 6,658,939 B2 | 12/2003 | Georgeson et al. | |
| 6,722,202 B1 | 4/2004 | Kennedy et al. | |
| 6,748,791 B1 | 6/2004 | Georgeson et al. | |
| 6,848,312 B2 * | 2/2005 | Georgeson | 73/627 |
| 6,910,380 B2 * | 6/2005 | Ogawa | 73/628 |
| 6,920,793 B2 * | 7/2005 | Stauffer | 73/630 |
| 6,924,642 B1 * | 8/2005 | Cho et al. | 324/240 |
| 7,055,389 B2 * | 6/2006 | Mueller | 73/620 |
| 7,231,826 B2 * | 6/2007 | Bossi et al. | 73/618 |
| 7,382,082 B2 * | 6/2008 | Bhardwaj | 310/357 |
| 2003/0055338 A1 * | 3/2003 | Steininger et al. | 600/459 |
| 2003/0154801 A1 | 8/2003 | Georgeson | |
| 2003/0210027 A1 | 11/2003 | Pedigo et al. | |
| 2004/0103721 A1 | 6/2004 | Georgeson | |
| 2005/0132809 A1 * | 6/2005 | Fleming et al. | 73/597 |
| 2006/0243051 A1 * | 11/2006 | Bui et al. | 73/618 |

OTHER PUBLICATIONS

*Non Destructive Testing.* http://www.aascworld.com/ndt-ttu.htm, Aug. 19, 2004, 3 pages.
*Inspection of In-Service Composite-Honeycomb Structures,* Aerospace Application Note, Rev.: Jan. 2002, R/D Tech.
*Probe Catalog 2003-2004,* Thru-Transmission Ultrasonics, NDT Engineering Corporation, R/D Tech Company, pp. 1-11.
*Air-Coupled Ultrasonic Inspection,* http://www.qmi-inc.com/AIRSCAN/htm, Aug. 19, 2004, 3 pages.
*Airscan® Transducer Specifications,* http://www.qmi-inc.com/Airscan%20TX%20Specifications.htm, Aug. 19, 2004, 18 pages.
U.S. Appl. No. 10/752,890, filed Jan. 7, 2004, In re: Bossi et al., entitled *Non-Destructive inspection Device for Inspecting Limited-Access Features of a Structure.*
U.S. Appl. No. 10/734,452, filed Dec. 12, 2003, In re: Bossi et al., entitled *Ultrasonic Inspection Device for Inspecting Components at Preset Angles.*
*High Speed Large Area Scanning Using Air-Coupled Ultrasound,* J. O. Strycek et al., http://www.qmi-inc.com/High%20Speed%20Large%20Area%20Scanning%20using%20air-coupled%2...,  Jun. 21, 2004, 5 pages.
*Ultran Labratories Transducers,* http://www.ultrangroup.com/products.php?printable=20, Aug. 19, 2004, 1 page.
*Conventional Transducers,* http://www.ultrangroup.com/products.php?section=9, Aug. 19, 2004, 2 pages.
*Non-Contact Transducers:<100kHz to 5MHz,* http://www.ultrangroup.com/trans.php, Aug. 19, 2004, 3 pages.
*Gas Matrix Peizoelectric,* http://www.ultrangroup.com/gmp.php?printable=7, Aug. 19, 2004, 3 pages.
*Gas Matrix Piezoelectric Composite GMP™ Transducers,* Second Wave Systems, 2003, 2 pages.
*IPass™,* http://www.ultrangroup.com/products.php?printable=1, Aug. 19, 2004, 1 page.
*IPass™ Technical Specs,* http://www.ultrangroup.com/products.php?printable=2, Aug. 19, 2004, 2 pages.
*Instant Picture Analysis System by Non-Contact Ultrasound,* SecondWave Systems, 2003, 2 pages.
*AirTech 4000,* http://www.ultrangroup.com/products.php?printable=3, Aug. 19, 2004, 1 page.
*Evolution of Piezoelectric Transducers to Full Scale Non-Contact Ultrasonic Analysis Mode,* M. C. Bhardwaj et al., Aug-Sep. 2004, World Conference on Non-Destructive Testing-2004, 9 pages.
*High Efficiency Non-Contact Transducers and a Very High Couping Piezoelectric Composite,* M. C. Bhardwaj, Aug-Sep. 2004, World Conference on Non-Destructive Testing-2004, 7 pages.

* cited by examiner

APPARATUS AND METHOD FOR AREA LIMITED-ACCESS THROUGH TRANSMISSION ULTRASONIC INSPECTION

CROSS-REFERENCED TO RELATED APPLICATIONS

The contents of co-pending applications filed concurrently herewith and entitled "Magnetically Attracted Inspecting Apparatus and Method Using a Fluid Bearing," "Magnetically Attracted Inspecting Apparatus and Method Using a Ball Bearing," "Alignment Compensator for Magnetically Attracted Inspecting Apparatus and Method," and "End Effector Inspection Apparatus and Method" are incorporated by reference in their entireties. The contents of U.S. Pat. No. 6,722,202 to Kennedy are incorporated by reference in its entirety.

The contents of co-pending application entitled "Non-Destructive Inspection Device for Inspecting Limited-Access Features of a Structure" by Bossi et al., assigned application Ser. No. 10/752,890 and filed Jan. 7, 2004, are incorporated by reference in its entirety.

FIELD OF THE INVENTION

The present invention relates generally to an apparatus and method for inspecting a structure and, more particularly, to an apparatus and method for inspecting a structure that uses airborne, non-contact ultrasonic transmission area transducers.

BACKGROUND

Non-destructive inspection (NDI) of structures involves thoroughly examining a structure without harming the structure or requiring significant disassembly of the structure. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or flaws in the structure. Inspection may be performed during manufacturing of a structure and/or once a structure is in-service. For example, inspection may be required to validate the integrity and fitness of a structure for continued use in manufacturing and future ongoing use in-service. However, access to interior surfaces is often more difficult or impossible without disassembly, such as removing a part for inspection from an aircraft.

Among the structures that are routinely non-destructively tested are composite structures, such as composite sandwich structures and other adhesive bonded panels and assemblies. In this regard, composite structures are commonly used throughout the aircraft industry because of the engineering qualities, design flexibility and low weight of composite structures, such as the stiffness-to-weight ratio of a composite sandwich structure. As such, it is frequently desirable to inspect composite structures to identify any flaws, such as cracks, voids or porosity, which could adversely affect the performance of the composite structure. For example, typical flaws in composite sandwich structures, generally made of one or more layers of lightweight honeycomb or foam core material with composite or metal skins bonded to each side of the core, include disbonds which occur at the interfaces between the core and the skin or between the core and a septum intermediate skin.

Various types of sensors may be used to perform non-destructive inspection. One or more sensors may move over the portion of the structure to be examined, and receive data regarding the structure. For example, a pulse-echo (PE), through- or thru-transmission (TT), or shear wave sensor may be used to obtain ultrasonic data, such as for thickness gauging, detection of laminar defects and porosity, and/or crack detection in the structure. Resonance, pulse echo or mechanical impedance sensors may be used to provide indications of voids or porosity, such as in adhesive bondlines of the structure. High resolution inspection of aircraft structure are commonly performed using semi-automated ultrasonic testing (UT) to provide a plan view image of the part or structure under inspection. While solid laminates may be inspected using one-sided pulse echo ultrasonic (PEU) testing, composite sandwich structures typically require through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure to be inspected such as opposite surfaces of a composite material. An ultrasonic signal is transmitted by at least one of the transducers, propagated through the structure, and received by the other transducer. Data acquired by sensors, such as TTU transducers, is typically processed by a processing element, and the processed data may be presented to a user via a display.

The non-destructive inspection may be performed manually by technicians who typically move an appropriate sensor over the structure. Manual scanning generally consists of a trained technician holding a sensor and moving the sensor along the structure to ensure the sensor is capable of testing all desired portions of the structure. In many situations, the technician must repeatedly move the sensor side-to-side in one direction while simultaneously indexing the sensor in another direction. For a technician standing beside a structure, the technician may repeatedly move the sensor right and left, and back again, while indexing the sensor between each pass. In addition, because the sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician in interpreting the displayed data. Thus, manual scanning of structures is time-consuming, labor-intensive, and prone to human error.

Semi-automated inspection systems have been developed to overcome some of the shortcomings with manual inspection techniques. For example, the Mobile Automated Scanner (MAUS®) system is a mobile scanning system that generally employs a fixed frame and one or more automated scanning heads typically adapted for ultrasonic inspection. A MAUS system, such as a MAUS-V system, may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician. However, for through-transmission ultrasonic inspection, a semi-automated inspection system requires access to both sides or surfaces of a structure which, at least in some circumstances, will be problematic, if not impossible, particularly for semi-automated systems that use a fixed frame for control of automated scan heads.

Automated inspection systems have also been developed to overcome the myriad of shortcomings with manual inspection techniques. For example, the Automated Ultrasonic Scanning System (AUSS®) system is a complex mechanical scanning system that employs through-transmission ultrasonic inspection. The AUSS system can also perform pulse echo inspections, and simultaneous dual frequency inspections. The AUSS system has robotically controlled probe arms that must be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. Conventional automated scanning systems, such as the AUSS-X system, therefore require access to both sides or surfaces of a structure which, at least in some circumstances, will be problematic, if not impossible, particularly for very large or small structures. In order to maintain the ultrasonic transmitter and receiver in proper alignment and spacing with one another and with the structure undergoing inspection, the AUSS-X system has a complex positioning system that provides motion control in ten axes. This requirement that the orientation and spacing of the ultrasonic transmitter and receiver be invariant with respect to one another and with respect to the structure undergoing inspection is especially difficult in conjunction with the inspection of curved structures.

Furthermore, manual, semi-automated, and automated scanning systems typically are limited in the size of a structure that can be inspected, generally limited to areas just a few meters square and typically limited to much smaller areas, although some larger, more complicated systems are available. Stiffness and weight limitations often restrict the distance a manual, semi-automated, or automated system may be able to extend inspection devices over a structure for inspection. Thus, large sandwich structures may not be capable of complete inspection.

In order to increase the rate or speed at which the inspection of a structure is conducted, the scanning system may include ultrasonic probes that have arrays of ultrasonic transmitters and receivers or may include arrays of ultrasonic probes each with one or more ultrasonic transmitter. As such, the inspection of the structure can proceed more rapidly and efficiently, thereby reducing the costs associated with the inspection. Unfortunately, the use of arrays of ultrasonic transmitters and receivers may be generally impractical during the scanning of structures which provide only limited access for inspection. Furthermore, coupling ultrasonic probes of an array may be complicated where the structure under inspection provides only limited access for inspection or may not be suited to being wetted, such as using water jets to provide water between the surface of the structure undergoing inspection and the ultrasonic transmitter or receiver in order to effectively couple ultrasonic signals into and out of the structure.

Accordingly, a need exists for an improved non-destructive inspection device and method to inspect a structure.

SUMMARY OF THE INVENTION

An improved non-destructive inspection device and method to inspect a structure which provides increased access to surfaces of a structure and allows for continuous inspection of large areas of a structure, including in-service, non-destructive inspection of sandwich structures, are provided according to the various embodiments of the present invention. In order to provide TTU signals through a limited-access structure, an area transducer, also referred to as an area ultrasonic testing (UT) transducer, such as a gas matrix piezoelectric (GMP™) area transducer, may be placed on or proximate to a surface of a structure to be inspected. An area transducer is used to provide a uniform area or sheet of ultrasonic signals over the surface of the area transducer and thereby into a part adjacent thereto. The uniform area ultrasonic signal transmits through the structure and may be received by a receiving transducer on the opposing side of the structure. A receiving transducer may be moved across the opposing surface corresponding to the surface coverage of the area transducer and uniform area of ultrasonic signals produced therefrom to collect TTU data about the structure under inspection such as to detect flaws in or damage to the structure.

An apparatus for inspecting a structure according to one embodiment of the present invention includes a receiving probe and an area transducer disposed on opposing surfaces of the structure being inspected. The area transducer is adapted to be capable of uniformly emitting ultrasonic signals across at least a portion of the area transducer and into the respective surface of the structure. The receiving probe includes an ultrasonic transducer for receiving ultrasonic signals emitted from the area transducer. The receiving probe may adapted to permit coupling of ultrasonic signals between the ultrasonic transducer of the receiving probe and the surface of the structure. Further, the receiving probe and/or the area transducer may include a contact mechanism, such as a fluid bearing, ball bearing, skid, wheel, or caster. The receiving probe may be moved across the opposing surface of the structure to receive the ultrasonic signals from the area transducer in order to scan the structure for inspection. An apparatus according to one embodiment of the present invention includes an area ultrasonic testing (UT) transducer including an airborne, non-contact ultrasonic testing transducer such as a gas matrix piezoelectric (GMP™) area transducer. Accordingly, an area transducer may be employed with a receiving probe, including a receiving transducer, where one or both of the area transducer and the receiving probe are controlled by a semi-automated or automated scanning system. A control system may be attached to the receiving probe for moving the receiving probe over a surface of the structure. Alternatively, or in addition, a control system may be adapted to position and hold and/or move the area transducer on the opposing surface of the structure, independently from the control of the motion of the receiving probe. For example, a control system may be magnetically attracted to the area transducer such that magnetic coupling between the control system and the area transducer causes movement of the area transducer when the control system is moved. Alternatively, the area transducer may be disposed against a surface of the structure under inspection using, for example, suction cups, vacuum cups, a holding stand, magnetic attraction of the area transducer to the structure itself, or magnetic attraction between the area transducer and the supporting mechanism on the opposite surface of the structure.

According to another aspect of the present invention, a method of inspecting a structure is provided. In this regard, a receiving probe is positioned proximate a first surface of the structure, and an area transducer is positioned proximate an opposed second surface of the structure. The area transducer uniformly emits ultrasonic signals across at least a portion of the area transducer and into a portion of the second surface of the structure. The receiving probe receives ultrasonic signals while moving along at least a portion of the first surface of the structure corresponding to the portion of the second surface into which the area transducer uniformly emits ultrasonic signals. The method may further include the steps of controlling the movement of the receiving probe over the first surface of the structure and moving the area transducer over the second surface. The method may further, or alternatively, include the step of controlling the movement of the area transducer over the second surface of the structure independent of the control of the movement of the receiving probe. The method of inspecting a structure according to an embodiment of the present invention may also include the step of establishing magnetic attraction to draw the area transducer toward the second surface of the structure, such as establishing magnetic attraction between the area transducer and a portion of a control system disposed proximate the first surface of the structure. Magnetic attraction between the area transducer and a portion of the control system may include the step of establishing magnetic coupling between the area transducer and the control system in order to move the area transducer over the second surface in response to corresponding movement of the control system over the first surface. Alternatively, a method of inspecting a structure according to a first embodiment of the present invention may include the step of holding the area transducer proximate the second surface of the structure, such as establishing a static suction between the area transducer and the second surface of the structure or magnetic attraction between the area transducer and the structure or a supporting mechanism on an opposing side of the structure from an area transducer.

Another embodiment of a method of inspecting a structure includes the steps of positioning a receiving probe proximate a first surface of the structure, positioning a first area transducer proximate an opposed second surface of the structure, uniformly emitting ultrasonic signals across at least a portion of the first area transducer and into a portion of the second surface of the structure, receiving ultrasonic signals at the receiving probe while moving the receiving probe along at least a portion of the first surface of the structure corresponding to the portion of the second surface into which the first area transducer uniformly emits ultrasonic signals, positioning a second area transducer proximate the second surface of the structure, uniformly emitting ultrasonic signals across at least a portion of the second area transducer and into a portion of the second surface of the structure adjacent to the portion of the second surface into which the first area transducer uniformly emits ultrasonic signals, and receiving ultrasonic signals at the receiving probe while moving the receiving probe along at least a portion of the first surface of the structure corresponding to the portion of the second surface into which the second area transducer uniformly emits ultrasonic signals. The method may further include the steps of repositioning the first area transducer on the second surface and repeating the step of receiving ultrasonic signals at the receiving probe while moving the receiving probe along at least a portion of the first surface of the structure corresponding to the portion of the second surface into which the first area transducer uniformly emits ultrasonic signals. The method may further comprise the steps of positioning the second area transducer on the second surface and repeating the step of receiving ultrasonic signals at the receiving probe while moving the receiving probe along at least a portion of the first surface of the structure corresponding to the portion of the second surface into which the second area transducer uniformly emits ultrasonic signals. A method of inspecting a structure may therefore include repeating the steps of repositioning the first and/or second area transducer(s) and scanning a portion of the structure corresponding to the repositioned first and/or second area transducer(s).

Additional embodiments of the method and apparatus of the present invention are capable of operating in an ultrasonic array mode using a plurality of receiving transducers, even in conjunction with the inspection of curved structures, thereby increasing the speed and efficiency with which such structures may be inspected and correspondingly reducing the cost associated with the inspection. Further, embodiments of the method and apparatus of the present invention permit an area transducer and a scanning system to be magnetically coupled to opposing surfaces of a structure, thereby reducing the necessary sophistication of the motion control system that is otherwise required by conventional TTU scanning systems in order to maintain ultrasonic probes in a predefined orientation and at a predefined spacing from the respective surface of a structure undergoing inspection and to maintain alignment between the probes or the sensors of the probes. Rather, by using an area transducer, a receiving probe may scan the corresponding area of the structure before the area transducer need be moved or another area transducer need be provided to perform continuous scanning.

These and other characteristics, as well as additional details, of the present invention are further described in the Detailed Description with reference to these and other embodiments.

BRIEF DESCRIPTION OF THE DRAWING(S)

Having thus described the invention in general terms, reference will now be made to the accompanying drawings, which are not necessarily drawn to scale, and wherein:

Figure 4A:
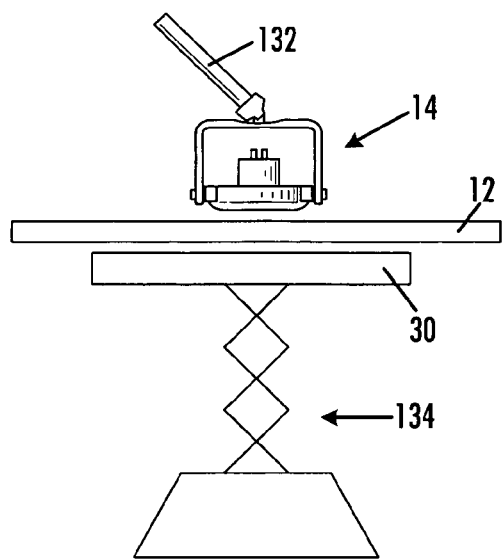
FIG. 4A is a schematic diagram of a receiving probe scanning a structure in coordination with an area transducer supported by a holding stand in accordance with an embodiment of the present invention.
Figure 4B:
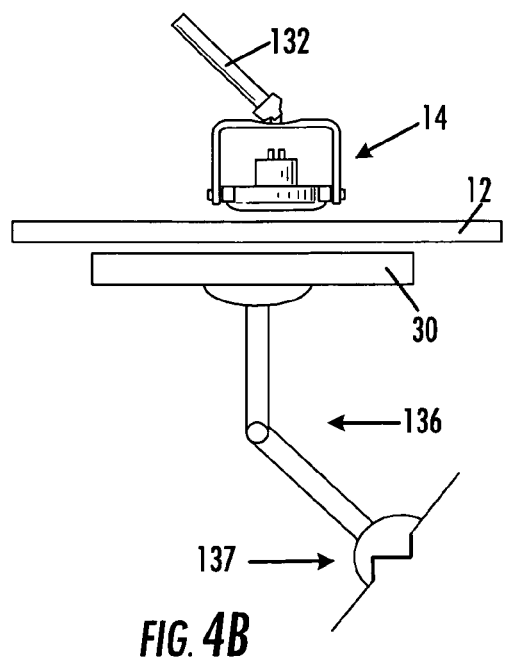
FIG. 4B is a schematic diagram of a receiving probe scanning a structure in coordination with an area transducer controlled by a control system in accordance with an embodiment of the present invention.
Figure 4C:
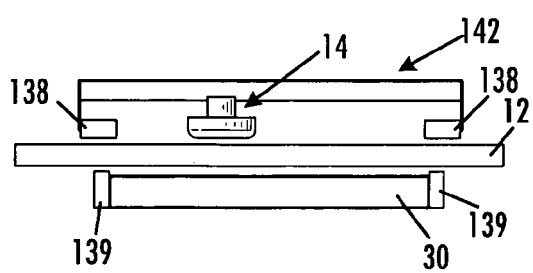
Figure 4D:
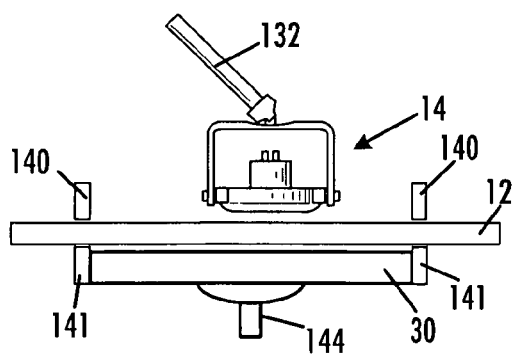

FIG. 4C is a schematic diagram of a receiving probe scanning a structure in coordination with an area transducer magnetically coupled to a scanning system controlling the receiving transducer in accordance with an embodiment of the present invention; and FIG. 4D is a schematic diagram of a receiving probe scanning a structure in coordination with an area transducer supported against the structure by magnetic attraction in accordance with an embodiment of the present invention.

DETAILED DESCRIPTION

The present inventions now will be described more fully with reference to the accompanying drawings, in which some, but not all embodiments of the invention are shown. Indeed, these inventions may be embodied in many different forms and should not be construed as limited to the embodiments set forth; rather, these embodiments are provided so that this disclosure will satisfy applicable legal requirements. Like numbers and variables refer to like elements and parameters throughout.

An apparatus of the present invention can inspect a variety of structures formed of various materials. Embodiments of the present invention provide capability for non-destructive inspection of structures with limited access, such as an inlet duct for an Unmanned Combat Air Vehicle (UCAV) or an F-35 tactical fighter where the inlet duct is fabricated as a composite sandwich structure, providing only limited access to the backside of the inlet duct for NDI. In embodiments where the apparatus relies to some extent upon the establishment of magnetic fields through the structure, however, the structure may be preferably non-magnetic, that is, the structure preferably has no magnetic permeability in at least some situations. Structures that may be inspected with an embodiment of an inspection device of the present invention may include, but are not limited to, composites, non-ferromagnetic metals (e.g. aluminum alloy, titanium alloy, or aluminum or titanium hybrid laminates such as GLARE or Ti/Gr), and polymers. It should be noted that the surfaces, and the material therebetween such as intermediate surfaces commonly referred to as septums, which collectively define the material through which the receiving probe and area transducer are magnetically coupled, preferably comprise a non-ferromagnetic material because the magnetic coupling between the receiving probe and area transducer would be diminished or eliminated by a ferromagnetic material located between the receiving probe and area transducer.

Figure 1:
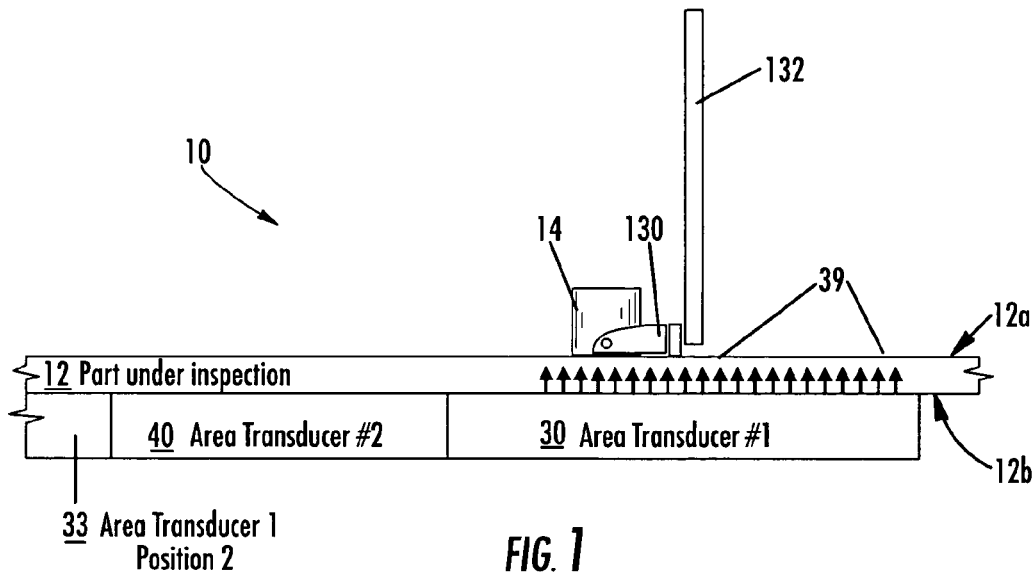
FIG. 1 is a schematic diagram of an apparatus according to an embodiment of the present invention having two area transducers and a receiving probe on opposing surfaces of a structure under inspection.

FIG. 1 is a schematic diagram of an apparatus according to an embodiment of the present invention having two area transducers and a receiving probe on opposing surfaces of a structure under inspection. The apparatus 10 includes a receiving probe 14 attached to an extension control arm 132, such as a yoke extension, by an attachment mechanism 130, such as a handle or yoke attachment. Although one mechanism for controllably positioning the receiving probe 14 proximate the part 12 is shown, the receiving probe 14 may be positioned proximate the part 12 and moved relative thereto in other manners. The receiving probe 14 scans a first surface 12a of a part 12 under inspection by moving the receiving probe 14 across the first surface 112a of the part 12 in order to receive ultrasonic signals 39 that propagate through the part 12. A first area transducer 30 and a second area transducer 40 are shown in FIG. 1 proximate a second surface 12b of the part 12 under inspection. The area transducers 30, 40 uniformly emit ultrasonic energy in the form of ultrasonic signals 39 that propagate through the part 12 for reception by a receiving probe 14. The first and second area transducers 30, 40 may be non-contact, airborne transducers such as gas matrix piezoelectric (GMP™) area transducers. An area transducer according to an embodiment of the present invention may use GMP™ area transducers manufactured by SecondWave Systems of The Ultran Group of Boalsburg, Pa. Area transducers with sufficient signal-to-noise and signal uniformity across the face of the area transducer for composite inspection application may be used with embodiments of the present invention. Currently, a GMP™ area transducer may be fabricated in virtually any flat shape up to three or four feet on a side, or even formed in large, non-uniform and/or complex shapes which may be selected in accordance with surfaces of structures desired for inspection. A GMP™ area transducer may be electrically connected to cabling typically used by ultrasonic instruments for use with an ultrasonic inspection system such as a TTU system. These and other types of area transducers are convenient for inspecting structures which may otherwise prohibit TTU inspection, such as in-service inspection of certain aircraft structures.

Area transducers, such as first and second area transducers 30, 40, may be positioned adjacent to one another on a surface of the structure, such as a second surface 12b of a part 12 under inspection, to provide uniform ultrasonic signals for continuous inspection, such as accomplished by moving a receiving probe 14 along an area of a first surface 12a of a part 12 corresponding to a portion of a second surface 12b of the part 12 proximate a first area transducer 30 and then continuously to an area of the first surface 12a of the part 12 corresponding to a portion of the second surface 12b of the part 12 proximate the second area transducer 40. To provide further continuous scanning of the part 12, when the receiving probe 14 completes scanning of the part 12 corresponding to the position of the first area transducer 30, the first area transducer 30 may be moved to a second position 33 adjacent to the opposing side of the second area transducer 40, thereby effectively leapfrogging the second area transducer. In such a manner, two or more area transducers may be used in sequence to provide continuous inspection of a part.

Embodiments of the present invention may employ control systems, or scanning systems, including manual, semi-automated, and automated scanning systems such as a MAUS-V or an AUSS-X control system. For example, a control system, such as a MAUS-V, may be used, to translate a receiving probe on a surface of a part under inspection. Further, an area transducer may be controlled by a control system, such as using a control arm 136 and control bridge 137 shown in FIG. 4B, or magnetically coupled to a control system, such as using magnets and/or ferromagnetic materials. For example, an area transducer may be magnetically coupled to translate on an opposing surface of a structure by means of a semi-automated or automated control system, such as an orthogonal grid scanning system 142 magnetically coupled with magnets 138 to magnets 139 affixed to the area transducer 30 on the opposite side of a structure 12 as shown in FIG. 4C. Accordingly, an area transducer of the embodiment is not stationary with respect to a surface of the structure under inspection, but is capable of traveling over the surface of the structure, such as corresponding to magnetically coupled movement of a control system.

For example, a thin linear GMP™ area transducer measuring between 0.5 and 2.0 inches may be magnetically coupled to a MAUS-V scanning system that also controls a receiving transducer on the opposing surface of a structure such that as the MAUS-V system moves forward with the receiving transducer, the magnetically coupled, thin linear GMP™ area transducer moves forward due to the magnetic coupling to the MAUS-V system. The MAUS-V system may include magnets, electromagnets, or ferromagnetic material that are magnetically coupled, and aligned, with magnets, electromagnets, or ferromagnetic material located on the area transducer to provide the movement in tandem. As used herein, the term "magnet" is inclusive of electromagnets. Alternatively, an area transducer may be held against a surface, such as a limited access interior surface, of a structure under inspection with suction cups, a vacuum or vacuum cups, magnetic attraction independent of the scanning system such as magnets at edges or corners of the area transducer and on the opposite side of the structure as shown in FIG. 4D, or like means for affixing the area transducer to the structure. For example, where magnetic attraction such as magnets 140, 141 at edges or corners of the area transducer 30 and on the opposite side of the structure 12 are used, a handle or other control point 144 may be used to translate the area transducer 30 over the surface of the structure 12. In such a case, the magnets 140, 141 supporting the area transducer 30 may be capable of translating over the surface of the structure 12 in coordination with a force applied to the control point 144 to move the area transducer 30 for further scanning in coordination with a receiving transducer 14 controlled by way of a control extension 132, such as a yoke attachment and extension. Further, because an area transducer does not require direct contact with the surface of the structure or a couplant for ultrasonic signals, an area transducer may be held proximate the surface of the structure, such as using a stand 134 as shown in FIG. 4A or a control system with a control arm 136 and control bridge 137 for holding an area transducer 30 in position on an opposing side of the structure 12 from where a receiving transducer 14 is operating as shown in FIG. 4B.

Figure 3:
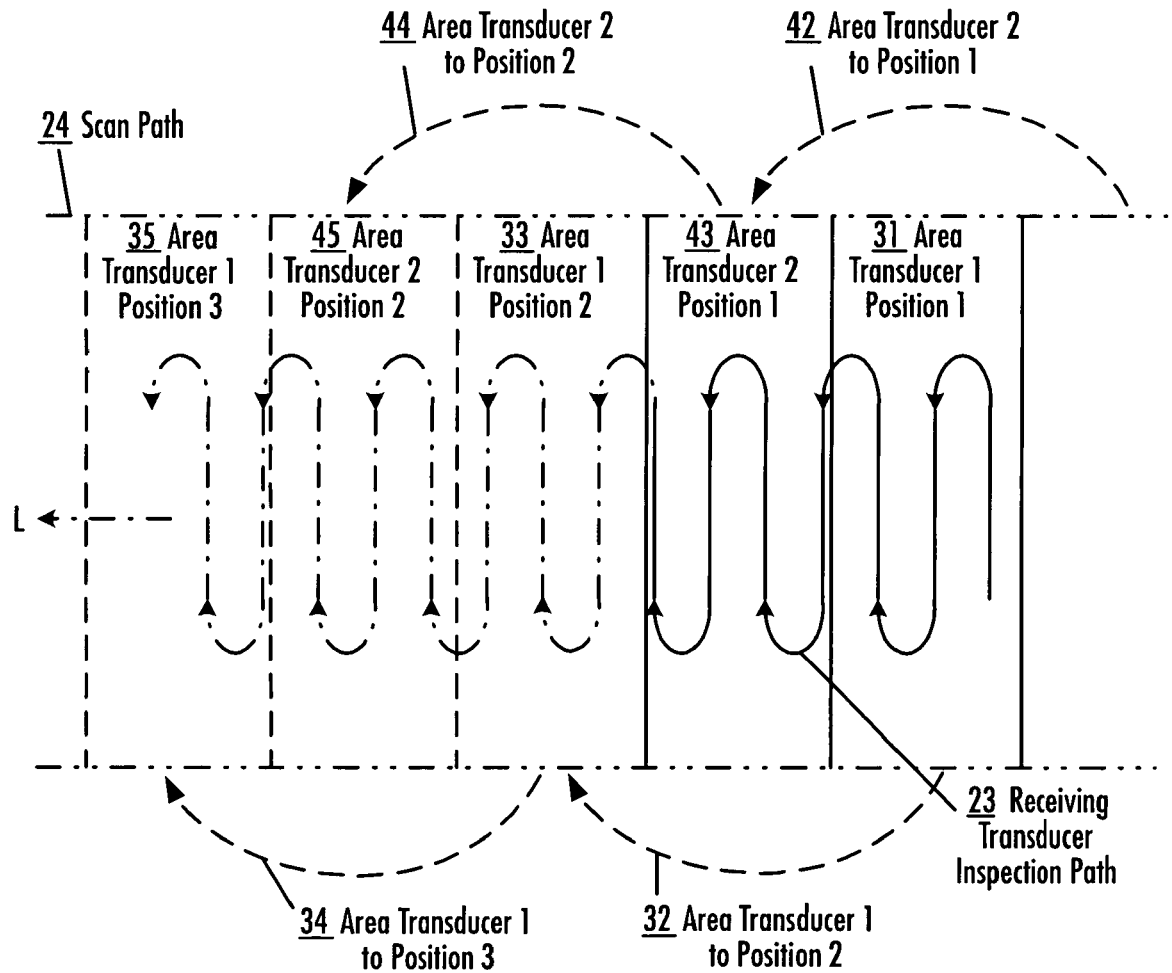
FIG. 3 is a schematic diagram of an inspection path of a structure under inspection using two area transducers and a receiving probe according to an embodiment of the present invention.

As described with respect to the apparatus 10 of FIG. 1, more than one area transducer may be used with a receiving probe to provide for continuous scanning. For example, one of the area transducers may be moved ahead of the area being scanned by the receiving probe while the other area transducer is sending a uniform ultrasonic signal for receipt by the receiving probe. Alternatively, a single area transducer may be used with a receiving probe to provide continuous scanning. For example, an AUSS-X system may be used with one control arm to control the movement of a receiving probe and a second control arm to control the movement of an area transducer. In such a manner, the first control arm may move the receiving probe along an inspection path 23 from side-to-side while translating in a linear direction L as shown in FIG. 3. The second control arm may move the area transducer in the same linear direction L as the receiving probe is moved.

Because an area transducer provides a uniform sheet or area of ultrasonic signals, more than one receiving transducer may be used such that multiple lines of TTU data may be acquired. For example, if using a side-to-side scanning motion with forward translation in a linear direction with multiple receiving transducers, the forward translation may proceed more rapidly than if only one receiving transducer were used. The increased linear translation accounts for the additional distance which may be traversed in the same period of time using an array of receiving transducers rather than a single receiving transducer. For example, if a single receiving transducer has a one inch scanning area, an array using three receiving transducers, each providing for one inch widths of scanning, could be translated linearly three times as fast as a one receiving transducer setup to account for receiving a three inch scan during side-to-side motion rather than a one inch scan using one receiving transducer. Because an area transducer provides uniform ultrasonic signals over a larger area, an array of receiving transducers can be used to capture ultrasonic signals from the area transducers over a large segment of the area transducer.

Receiving transducers may be airborne, non-contact transducers or coupled transducers such as water-coupled transducers. However, because an area transducer is typically an airborne, non-contact area transducer, no water or other couplant may be required on the surface of the structure under inspection proximate to the area transducer. Avoiding a couplant with an area transducer may be advantageous such as when scanning structures such as the interior of a structure which may not be inclined to being wetted or exposed to another couplant. An area transducers may, however, translate over a surface of a structure using a contact member, such as wheels, spherical bearings, Teflon® skids, water bearings, and the like. The selection of contact members may be based upon such considerations such as whether the area transducer is intended to contact and/or rest against the surface or whether a holding stand or control system may be used to hold the area transducer proximate to but not against the surface. At a minimum, however, the structure must provide access for the area transducer to be placed into position for scanning.

Figure 2:
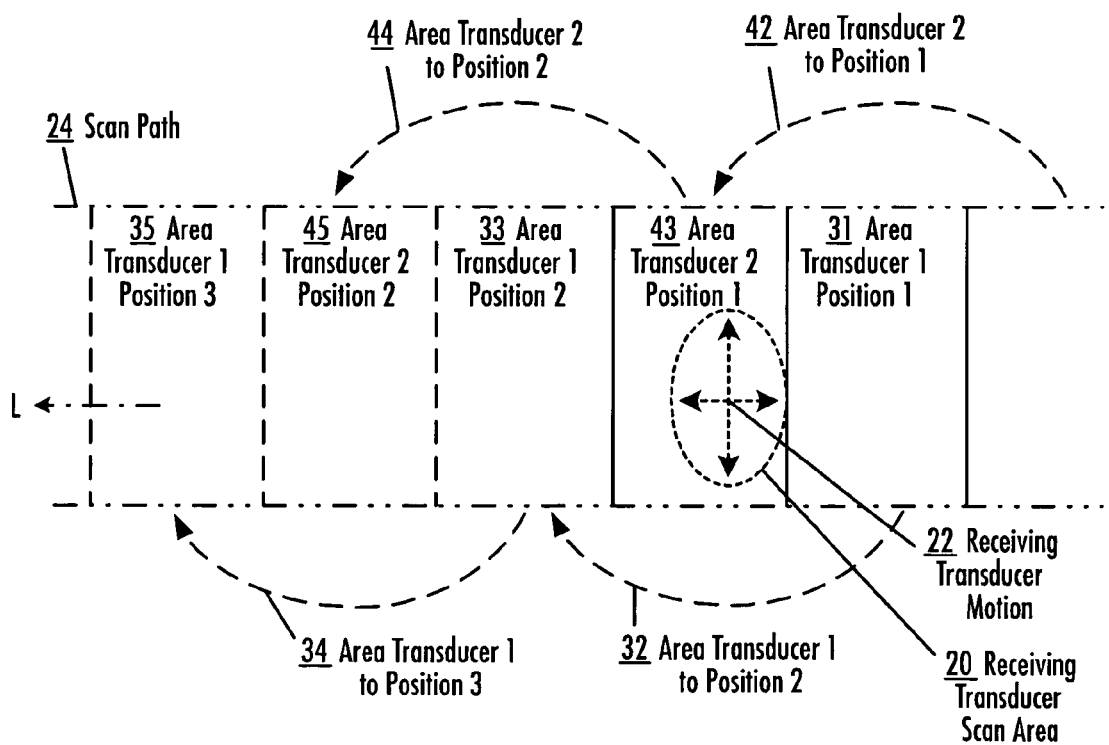
FIG. 2 is a schematic diagram of a scan path of a structure under inspection using two area transducers and a receiving probe according to an embodiment of the present invention.

FIG. 2 is a schematic diagram of a scan path of a structure under inspection using two area transducers and a receiving probe according to an embodiment of the present invention. The depiction in FIG. 2 is an example of the type of a scan path 24 which may be produced using an apparatus with two area transducers, such as the apparatus 10 shown in FIG. 1 with the first area transducer 30 and the second area transducer 40. As shown in FIG. 2, each of the area transducers are moved to an alternating sequence of positions with the first area transducer being sequentially placed in positions 31, 33, and 35 and the second area transducer being sequentially placed in positions 43 and 45. For example, a first area transducer in a first position 31 may be moved 32 to a subsequent position 33 in a sequence in front of a second area transducer in first position 43 once the area underlying the first area transducer in the first position has been scanned. Subsequently, the second area transducer may be moved 44 from a first position 43 to a second position 45. Similarly, thereafter, the first area transducer may be moved 34 from the second position 33 to a third position 35. The sequence of positions 31, 43, 33, 45, 35 for the area transducers produces the scan path 24. While an area transducer is positioned in the scan path 24, a receiving transducer may move 22 to produce a receiving transducer scan area 20 in alignment with the positions 31, 43, 33, 45, 35 of the area transducers. A receiving transducer may be moved 22 such that the scan area 20 of the receiving transducer continuously scans through the scan path 24 as the area transducers are moved to subsequent positions 31, 43, 33, 45, 35. For example, FIG. 3 is a schematic diagram of an inspection path of a structure under inspection using two area transducers and a receiving probe according to an embodiment of the present invention. By following a receiving transducer inspection path 23, a receiving transducer, or array of receiving transducers, may continuously scan portions of a surface of a structure under inspection corresponding to positions 31, 43, 33, 45, 35 of at least one area transducer proximate the opposing surface of the structure under inspection. For example, as the receiving transducer inspection path 23 completes inspection of that portion of the structure corresponding to a first position 31 of a first area transducer and begins inspection of that portion of the structure corresponding to a first position 43 of a second area transducer, the first area transducer may be moved 32 into a second position 33 for the first area transducer. As the receiving transducer inspection path 23 completes the scan of that portion of the structure corresponding to the first position 43 of the second area transducer and begins inspection of that portion of the structure corresponding to the second position 33 of the first area transducer, the second area transducer may be moved 44 to a second position 45 for the second area transducer.

Embodiments of the present invention may be used with an inspection device similar to that disclosed in the referenced co-pending applications or in U.S. Pat. No. 6,722,202 directed to magnetically attracted probes for inspection of a structure, the contents of which are hereby incorporated by reference in its entirety, including as non-limiting examples methods and apparatuses for inspecting structures and a structure and operation of magnetically attracted probes for inspection of a structure. The shape and size of an inspection probe, and housing thereof, which may be used with the present invention is not limited to the specific embodiments describe and disclosed herein or in the U.S. Pat. No. 6,722, 202 patent or referenced co-pending applications, but may be any shape or size capable of operating in accordance with the present invention.

The receiving probe includes an ultrasonic transducer such as a 1 MHz immersion transducer from Agfa/Krautkramer of Lewistown, Pa. In this regard, embodiments of the present invention provide for the inspection of the structure by means of a through transmission technique in coordination with ultrasonic signals uniformly emitted from an area transducer and transmitted into the structure and thereafter received by the ultrasonic transducer of the receiving probe. By analyzing the ultrasonic signals following transmission through the structure, various flaws within the structure, such as cracks, voids and/or porosity, may be identified as known to those skilled in the art.

As described, in order to facilitate contact with respective surfaces of a structure under inspection, and to avoid any undesirable damage or other marring of the respective surfaces of the structure as the result of contact, receiving probes and area transducers can each include at least one contact member, such as a fluid bearing, ball bearing, skid, wheel, or caster, which can be used in conjunction with or independently from other contact members, such as a fluid bearing used with skids. Typically, the contact member(s) extend outwardly from the face or surface of the receiving probe or area transducer that faces the respective surface of the structure. Skids may include a Teflon® material available from E.I. DuPont Nemours and Company of Wilmington, Del., on a surface of the skid for contact with the surface of the structure being inspected and to provide for translation thereacross. Skids may be beneficial for fluid bearing embodiments of receiving probes and area transducers of the present invention such as to prevent damage or marring of a surface of a structure under test when initially placing a receiving probe or area transducer on the structure or magnetically coupling a receiving probe and/or area transducer on opposite sides of the part, particularly when the fluid bearing may not be in use, such as before fluid is provided or after fluid is stopped flowing for the fluid bearing. Alternatively, a probe may include one or more ball and socket bearings that contact the respective surface of the structure and that permit the probe to ride therealong when not using a fluid bearing. Fluid bearings, such as water bearing and air bearings, and ball bearings may be used to maintain the spacing and orientation of the probes. Water, air, or ball bearings may be used to reduce the friction between the inspection probe and the surface of the structure under inspection, such as to displace the probe from contacting the surface of the structure using hydraulic flotation or a hydrostatic bearing. Further, use of bearing contact between the inspection probe and the surface of the structure may prevent scratching of soft skins or denting of panels of the skins. Use of bearing contact may also provide smooth translation of an inspection probe over the surface of a structure to allow an inspection probe to maintain an intended direction, maintain alignment of transducers and/or receivers in inspection probes, and allow continuous scanning of a surface regardless of size, smoothness, or flatness of the surface.

Embodiments of the present invention permit continuous scanning techniques such as manual scanning of an entire surface and point-by-point or grid-type inspection methods that may commonly be used for manual, semi-automated, and automated scanning systems. An inspection area may be as large as the area over which the area transducer uniformly emits ultrasonic signals or as large as the area over which an area transducer may be moved or multiple area transducers may be positioned and/or moved such as to provide for an inspection area as large as the entire structure. Enabling inspection of areas, even as large as an entire structure, rather than discrete points of inspection improves the ability to detect imperfections in the structure and ensure structural integrity of a part.

Further, embodiments of the present invention may be scaled and adapted as desired, such as to be driven by a MAUS or AUSS system, a fixed or movable orthogonal grid-type control system, or other automated or semi-automated system.

If water, or another liquid, is used with an embodiment of the present invention, the probe or apparatus will likely include or be used with a reservoir to collect the expelled water and, possibly, recycle the water. For example, if water is used as a couplant and/or to provide a water bearing for a probe, the water that spills or drains off of a part may be collected and recycled to be used again as a couplant or for a water bearing. Similarly, if a gas is used to provide a fluid bearing, a reservoir such as a containment housing, a sealed room, or the like, may be used to capture and recycle the gas. For example, a sealed chamber may be used to surround the structure being inspected and the probes such that the couplant may be present in the sealed chamber and may be pumped through the probe to be used as a fluid bearing and/or a pressurized gas couplant. Various considerations may impact a selection of a couplant or fluid for a bearing, such as whether internal systems of a structure can be exposed to the fluid such as water, the availability of a fluid, and the difficulty to maintain, collect, and/or recycle a fluid. Similar considerations may impact the selection of the type of inspection method or sensor to be used. For example, non-contact air ultrasonic transducers typically require lower frequency signals compared to water-coupled ultrasonic transducers. Thus, although water may be a better couplant than air, a system using the pressurized air of an air bearing as a couplant may be selected to eliminate the complications associated with using water with an inspection system. An embodiment of the present invention may use one type of a bearing contact for the receiving probe and the same or a different type of bearing contact for the area transducer, such as where the area transducer is located inside a part and proximate components which may not readily accept the presence of certain bearing contact such as a water bearing. For example, a receiving probe may use a water bearing and an area transducer may use an air bearing. Alternatively, the receiving probe may use an air bearing and the area transducer may use a water bearing. Regardless of the type of fluid selected for a fluid bearing, the additional elements of a fluid bearing system such as hoses add weight to a probe, particularly water hoses which may make an air bearing more appropriate for some inspection situations.

Accordingly, provided are apparatuses and methods for inspecting a structure which include receiving probes and area transducers disposed proximate opposite surfaces of a structure under inspection. An area transducer uniformly emits ultrasonic signals over an area which may be scanned by a receiving probe without corresponding movement of the area transducer. An area transducer may be moved over the surface of the structure or repositioned to provide additional inspection area for the receiving probe to scan, including to provide for continuous inspection. Multiple area transducers may be used in sequence to provide for continuous inspection. Multiple receiving probes may be used, independently or collectively as an array, to increase inspection of a structure, taking advantage of the large area of ultrasonic signals emitted by one or more area transducers.

Many modifications and other embodiments of the inventions set forth will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed, they are used in a generic and descriptive sense only and not for purposes of limitation.

That which is claimed:

1. An apparatus for inspecting a structure comprising:
   a receiving probe structured to be disposed proximate a first surface of the structure, said receiving probe comprising an ultrasonic transducer configured to inspect the structure as said receiving probe is moved over the first surface of the structure; and
   an area transducer structured to be disposed proximate an opposed second surface of the structure and configured to uniformly emit ultrasonic signals across at least a portion of the area transducer;
   wherein said receiving probe is configured to inspect the structure as said receiving probe is moved over the first surface of the structure and is moved relative to the portion of the area transducer configured to uniformly emit ultrasonic signals.

2. The apparatus of claim 1, further comprising a control system operably attached to said receiving probe and adapted to be capable of moving said receiving probe over the first surface of the structure.

3. The apparatus of claim 2, wherein said control system and said area transducer are magnetically attracted to draw the control system and the area transducer toward the first and second surface of the structure, respectively.

4. The apparatus of claim 3, wherein said magnetic attraction provides magnetic coupling between said control system and said area transducer, wherein said magnetic coupling causes said area transducer to be moved over the second surface of the structure in response to corresponding movement of said control system over the first surface of the structure independent of the movement of said receiving probe by said control system.

5. The apparatus of claim 2, wherein said control system is independently operably attached to said area transducer and adapted to be capable of holding said area transducer proximate the second surface of the structure, and wherein said control system is adapted to be capable of moving said receiving probe over at least a portion of the first surface corresponding to the portion of the second surface proximate the area transducer.

6. The apparatus of claim 5, wherein said control system is further adapted to be capable of moving said area transducer over said second surface of the structure independent of the movement of said receiving probe by said control system.

7. The apparatus of claim 1, wherein said area transducer is disposed proximate the second surface of the structure by at least one of the affixing mechanisms selected from the group consisting of suction cups, vacuum cups, a holding stand, magnetic attraction of the area transducer to the structure, and magnetic attraction between the area transducer and a supporting mechanism disposed on the first surface of the structure.

8. The apparatus of claim 7, wherein said affixing mechanism is magnetic attraction between the area transducer and a supporting mechanism disposed on the first surface of the structure, wherein said supporting mechanism comprises at least one magnet and said area transducer comprises at least one magnet or ferromagnetic material.

9. The apparatus of claim 7, wherein said affixing mechanism is magnetic attraction between the area transducer and a supporting mechanism disposed on the first surface of the structure, wherein said area transducer comprises at least one magnet and said supporting mechanism comprises at least one magnet or ferromagnetic material.

10. The apparatus of claim 1, wherein said receiving probe and said area transducer are magnetically attracted to draw the receiving probe and the area transducer toward the first and second surface of the structure, respectively.

11. The apparatus of claim 1, wherein at least one of said receiving probe and said area transducer comprise a contact mechanism selected from the group consisting of a fluid bearing, a ball bearing, a skid, a wheel, and a caster.

12. The apparatus of claim 1, wherein said receiving probe is adapted to be capable of coupling ultrasonic signals between said ultrasonic transducer and the first surface of the structure.

13. The apparatus of claim 1, further comprising a plurality of receiving probes for cooperating with said receiving probe to form an array of receiving probes structured for being disposed proximate a first surface of the structure, each of said receiving probes of said array comprising an ultrasonic transducer for inspecting the structure as said array is moved over the first surface of the structure.

14. The apparatus of claim 1, wherein said area transducer comprises a non-contact gas matrix piezoelectric area transducer.

15. A method of inspecting a structure comprising:
   positioning a receiving probe proximate a first surface of the structure and an area transducer proximate an opposed second surface of the structure;
   uniformly emitting ultrasonic signals across at least a portion of the area transducer and into a portion of the structure; and
   receiving ultrasonic signals at the receiving probe while moving the receiving probe along at least a portion of the first surface of the structure corresponding to the portion of the structure into which the area transducer uniformly emits ultrasonic signals and while moving the receiving probe relative to the portion of the area transducer uniformly emitting ultrasonic signals.

16. The method of claim 15, further comprising the step of controlling the movement of the receiving probe over the first surface of the structure.

17. The method of claim 16, further comprising the step of moving the area transducer over the second surface.

18. The method of claim 17, further comprising the step of controlling the movement of the area transducer over the second surface of the structure independent of the step of controlling the movement of the receiving probe.

19. The method of claim 15, further comprising the step of establishing magnetic attraction to draw the area transducer toward the second surface of the structure.

20. The method of claim 19, wherein the step of establishing magnetic attraction to draw the area transducer toward the second surface comprises the step of establishing magnetic attraction between the area transducer and a portion of a control system disposed proximate the first surface of the structure.

21. The method of claim 20, wherein said step of establishing magnetic attraction between the area transducer and a portion of a control system comprises the step of establishing magnetic coupling between the area transducer and the control system to move the area transducer over the second surface in response to corresponding movement of the control system over the first surface independent of movement of the receiving probe.

22. The method of claim 19, wherein the step of establishing magnetic attraction to draw the area transducer toward the second surface comprises the step of establishing magnetic attraction between the area transducer and the receiving probe.

23. The method of claim 19, wherein the step of establishing magnetic attraction to draw the area transducer toward the second surface comprises the step of establishing magnetic attraction between the area transducer and a supporting mechanism disposed proximate the first surface of the structure.

24. The method of claim 15, further comprising the step of holding the area transducer proximate the second surface of the structure.

25. The method of claim 24, wherein the step of holding the area transducer comprises the step of establishing a suction between the area transducer and the second surface of the structure, wherein a characteristic of the suction is selected from the group consisting of static suction and vacuum suction.

26. The method of claim 24, wherein the step of holding the area transducer comprises the step of establishing magnetic attraction between the area transducer and the structure.

27. The method of claim 15, further comprising the step of coupling ultrasonic signals between the receiving probe and the first surface of the structure.

28. A method of inspecting a structure comprising:
positioning a receiving probe proximate a first surface of the structure and a first area transducer proximate an opposed second surface of the structure;
emitting ultrasonic signals across at least a portion of the first area transducer and into a portion of the structure;
receiving ultrasonic signals at the receiving probe while moving the receiving probe along at least a portion of the first surface of the structure corresponding to the portion of the second surface into which the first area transducer emits ultrasonic signals;
positioning a second area transducer proximate the second surface of the structure and proximate the first area transducer;
emitting ultrasonic signals across at least a portion of the second area transducer and into a portion of the structure; and
receiving ultrasonic signals at the receiving probe while moving the receiving probe along at least a portion of the first surface of the structure corresponding to the portion of the second surface into which the second area transducer emits ultrasonic signals.

29. The method of claim 28, further comprising the steps of:
repositioning the first area transducer on said second surface relative to the second area transducer;
emitting ultrasonic signals across at least a portion of the repositioned first area transducer following the repositioning; and
receiving ultrasonic signals at the receiving probe while moving the receiving probe along at least a portion of the first surface of the structure corresponding to the portion of the structure into which the repositioned first area transducer emits ultrasonic signals.

30. The method of claim 29, further comprising the steps of:
repositioning the second area transducer on said second surface relative to the repositioned first area transducer;
emitting ultrasonic signals across at least a portion of the repositioned second area transducer following the repositioning; and
receiving ultrasonic signals at the receiving probe while moving the receiving probe along at least a portion of the first surface of the structure corresponding to the portion of the structure into which the repositioned second area transducer emits ultrasonic signals.

31. The method of claim 30, further comprising the step of repeating the steps of (a) repositioning the first area transducer on said second surface relative to the second area transducer; (b) emitting ultrasonic signals across at least a portion of the repositioned first area transducer following the repositioning; (c) receiving ultrasonic signals at the receiving probe while moving the receiving probe along at least a portion of the first surface of the structure corresponding to the portion of the structure into which the repositioned first area transducer emits ultrasonic signals; (d) repositioning the second area transducer on said second surface relative to the repositioned first area transducer; (e) emitting ultrasonic signals across at least a portion of the repositioned second area transducer following the repositioning; and (f) receiving ultrasonic signals at the receiving probe while moving the receiving probe along at least a portion of the first surface of the structure corresponding to the portion of the structure into which the repositioned second area transducer emits ultrasonic signals.

32. The method of claim 28, further comprising the step of controlling the movement of the receiving probe over the first surface of the structure.

33. The method of claim 32, further comprising the step of controlling the positioning of the first and second area transducers over the second surface of the structure independent of the movement of the receiving probe.

34. The method of claim 28, further comprising the step of establishing magnetic attraction to draw at least one of the first area transducer and the second area transducer toward the second surface of the structure.

35. The method of claim 34, wherein the step of establishing magnetic attraction to draw the respective area transducer toward the second surface comprises the step of establishing magnetic attraction between the respective area transducer and a portion of a control system disposed proximate the first surface of the structure.

36. The method of claim 35, wherein said step of establishing magnetic attraction between the respective area transducer and a portion of a control system comprises the step of establishing magnetic coupling between the respective area transducer and the control system to move the respective area transducer over the second surface in response to corresponding movement of the control system over the first surface independent of movement of the receiving probe.

37. The method of claim 34, wherein the step of establishing magnetic attraction to draw the respective area transducer toward the second surface comprises the step of establishing magnetic attraction between the respective area transducer and a supporting mechanism disposed proximate the first surface of the structure.

38. The method of claim 28, further comprising the step of holding at least one of the first area transducer and second area transducer proximate the second surface of the structure.

39. The method of claim 38, wherein the step of holding the respective area transducer comprises the step of establishing a suction between the respective area transducer and the second surface of the structure, wherein a characteristic of the suction is selected from the group consisting of static suction and vacuum suction.

40. The method of claim 38, wherein the step of holding the respective area transducer comprises the step of establishing magnetic attraction between the respective area transducer and the structure.

41. The method of claim 28, further comprising the step of coupling ultrasonic signals between the receiving probe and the first surface of the structure.

* * * * *